(12) United States Patent
Zhang et al.

(10) Patent No.: US 6,399,087 B1
(45) Date of Patent: Jun. 4, 2002

(54) PROPOFOL FORMULATION WITH ENHANCED MICROBIAL INHIBITION

(75) Inventors: Jack Yongfeng Zhang; Jie Fei Ding; Mary Zi-ping Luo, all of Rancho Cucamonga, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 0 days.

(21) Appl. No.: 09/745,018

(22) Filed: Dec. 20, 2000

(51) Int. Cl.⁷ .................. A01N 25/00; A01N 31/05; A01N 31/08; A61K 35/78
(52) U.S. Cl. .................. 424/405; 424/757; 514/731; 514/816; 514/938
(58) Field of Search .................. 514/816, 731, 514/938; 424/405, 757

(56) References Cited

U.S. PATENT DOCUMENTS 6,100,302 A * 8/2000 Pejaver et al. .............. 514/731

* cited by examiner

Primary Examiner—Christopher R. Tate
Assistant Examiner—Randall Winston
(74) Attorney, Agent, or Firm—Albert O. Cota

(57) ABSTRACT

A sterile, stable pharmaceutical formulations of oil-in-water emulsions of Propofol containing no preservative are provided that comprise optimal amounts of egg lecithin and soybean oil, with a suitable pH range to prevent significant growth of microorganisms for at least 24 hours after adventitious, extrinsic contamination. The lower pH in the formulation has shown the most antimicrobial activity. The reduced amount of fat in the formulation also allows chronic sedation over extended periods of time with a reduced chance of fat overload in the blood.

14 Claims, 4 Drawing Sheets

PROPOFOL FORMULATION WITH ENHANCED MICROBIAL INHIBITION

TECHNICAL FIELD

The invention generally pertains to optimized pharmaceutical formulations of a drug known as Propofol, which is an intravenous anesthetic with enhanced microbial inhibition. More particularly, the invention pertains to an optimized Propofol emulsion formulation that is shown to be bacteriostatic or fungistatic and in some formulations bactericidal and fungicidal without using a preservative or other antimicrobial agents.

BACKGROUND ART

Propofol (2,6-Diisopropylphenol) is a well-known and widely used intravenous anesthetic agent. For example, in intensive care units (ICU) where the duration of treatment may be lengthy, Propofol has the advantage of a rapid onset after infusion or bolus injection plus a very short recovery period of several minutes, instead of hours.

Propofol is a hydrophobic, water-insoluble oil. To overcome the solubility problem, it must be incorporated with solubilizing agents, surfactants, solvents, or an oil in water emulsion. There are a number of known Propofol formulations, such as disclosed in U.S. Pat. Nos. 4,056,635, 4,452,817 and 4,798,846 all of which are issued to Glen and James.

There are two major problems associated with the formulations described in the above patents: (1) the risk of microbial contamination due to the high nutrient content and lack of antimicrobial preservatives. Studies by Arduino, et al., 1991; Sosis & Braverman, 1993; and PDR, 1995, have shown that a Propofol emulsion formulated without preservatives will grow bacteria and present a risk of bacterial contamination. (2) Hyperlipidemia in patients undergoing long-term ICU sedation due to a large amount of fat content. Studies have shown that triglyceride overload can become a significant problem when a 1% Propofol/10% soybean oil emulsion is used as the sole sedative for a long period of ICU sedation by Gottardis, et al., 1989; DeSoreruer, et al., 1990; Lindholm, 1992; and Eddieston, et al, 1991.

To solve the problem of bacterial contamination of Propofol emulsion, the following patented formulations of Propofol have been developed:

| PATENT NO. | INVENTOR | ISSUED |
| --- | --- | --- |
| 5,637,625 | Duncan H. Haynes | 10 June 1997 |
| 5,714,520 | Christopher B. J., et al | 3 February 1998 |
| 6,028,108 | Mary M. G. | 22 February 2000 |
| 6,100,302 | Satish K. P., et al | 8 August 2000 |
| PCT W.O. 99/396,96 | Mirejovsky D., et al | 12 August 1999 |
| PCT W.O. 00/24376 | Mary T., et al | 4 May 2000 |

The formulations described in U.S. Pat. No. 5,714,520 is sold as DIPRIVAN$^{(R)}$ and comprises a sterile, pyrogen-free emulsion containing 1% (W/v) Propofol in 10% (w/v) soybean oil. The formulation also contains 1.2(w/v) egg lecithin as a surfactant, 2.25% (w/v) glycerol to make the formulation isotonic, sodium hydroxide to adjust the pH, and EDTA 0.0055% (w/v) as a preservative. This formulation prevents no more than a 10-fold increase against gram negative (such as Pseudomonas aeruginosa and Escherichia coli) and gram positive (Staphylococcus aureus) bacteria, as well as yeast (such as Candida albicans) over a twenty-four hour period. However, EDTA, which is a metal ion chelator, remove cations like calcium magnesium and zinc. This can be potentially dangerous to some patients with low calcium or other low cation levels, and especially critical for ICU patients.

In U.S. Pat. No. 6,028,108 the Propofol formulation contains pentetate 0.0005% (w/v) as a preservative to prevent microbial contamination. Pentetate is a metal ion chelator similar to EDTA and therefore represents the same potential danger.

The formulation described in W.O. Patent No. 99/39696, is generic Propofol containing 0.25 mg/mL sodium metabisulfite as a preservative to prevent microbial growth. At 24 hours there is no more than a one log increase. Recently, P. Langevin, 1999, has expressed concern that generic Propofol containing 0.25 mg/mL sodium metabisulfite, infused at a rate of 50 ug/kg/min, will result in sulfite administration approaching the toxic level (i.e., near the LD50 for rats) in about 25 hours. Particularly, the addition of sulfites to this drug is worrisome for the potential effects to the pediatric population.

The formulation described in PCT W.O. Patent No. 00/24376 is a formulation having an antimicrobial agent, which is a member selected from the group consisting of benzyl alcohol and sodium ethylenediamine tetraacetate, benzethonium chloride; and benzyl alcohol and sodium benzoate. The formulation contains EDTA, which was mentioned as related to the side effect above. Benzyl alcohol is linked to adverse reactions reported by Evens and Lopez-Herce, et al. The formulation may be unsafe upon administration, particularly to those patients who need an extended period of ICU sedation.

The formulation described in U.S. Pat. No. 5,637,625 is of phospholipid-coated microdroplets of Propofol, containing 6.8% Propofol with no soybean oil. However, it is believed that this formulation may increase injection site pain to an unacceptable level during administration.

The formulation described in U.S. Pat. No. 6,100,302 is an emulsion of Propofol that contains 1–3% of soybean oil to prevent against accidental microbial contamination during long-term IV infusions due to an increased availability of Propofol. However, the formulation containing 2% of soybean oil can not prevent a less than one log increase for E. coli at 48 hours.

Particularly, the formulation comprising 3% of soybean oil has more than a 10-fold increase for E. coli at 24 hours, which fails to meet current industry standards to prevent no more than one log increase in microbial growth at 24 hours. It appears that upon administration this formulation may also increase the problem of pain on injection due to a higher partition of Propofol in the aqueous phase. This has been studied by M. Eriksson, et al 1997.

The problems described above are addressed by developing an optimized Propofol formulation provided in the present invention. Propofol is a hindered phenol. Phenol shows substantial antimicrobial activity in low pH solutions (Arthur H. Kibbe, 2000). It has been found in this invention that a Propofol formulation with a low pH is more effective in inhibiting microbial growth as shown in FIGS. 2 and 3. Also, the lower pH in the formulation reduces the concentration of Propofol anions. As Propofol is a weak acid with a pKa of 11, such an effect would result in reduced pain on injection, which has been studied by W. Klement, et al., 1991 and J. Babl 1995.

Egg lecithin is mainly used in pharmaceutical products as a dispersing, emulsifying, and stabilizing agent. The lecithin is also used as component of enteral and paranteral nutrition formulations, Arthur H. Kibbe, 2000.

It has been also found that in this invention a Propofol formulation containing a reduced amount of egg lecithin results in a significant increase in the ability to be antimicrobial as shown in FIG. 4. The soybean oil is also source of nutrition to support the microbial growth. As shown in FIG. 2, this invention shows that the high amount of soybean oil in the formulation increases microbial growth.

Thus, it has been found that the preservative-free, optimized Propofol formulation of this invention addresses the prior art problems to the point where the problems are eliminated or at the least are substantially reduced.

DISCLOSURE OF THE INVENTION

Accordingly, the present invention provides an optimized, sterile formulation of Propofol for parenteral administration containing a reduced amount of egg lecithin and soybean oil triglycerides. The formulation is preferably comprised of an oil in water emulsion with a particle range of about 200 to 400 nonometers in diameter, in which the Propofol is dissolved in a water-immiscible solvent such as soybean oil, and stabilized by a surfactant such as egg lecithin. The low amount of lecithin and soybean oil, with a pH 5.0–7.5 range for the Propofol formulation, has a number of advantages:

(1) eliminating of preservatives,
(2) providing formulations with excellent exhibition of antimicrobial activity compared to formulations with higher amount of lecithin and oil solvent emulsion containing preservatives,
(3) a reduced risk of hyperlipidemia in patients, and
(4) the low pH of the Propofol formulation may reduce the Propofol-induced pain on injection, as shown in studies by Klement, et al., 1991; Babl, et al, 1995 and Eriksson, et al., 1997.

These and other objects and advantages of the present invention will become apparent from the, subsequent detailed description of the preferred embodiment and the appended claims taken in conjunction with the accompanying drawings.

BEST MODE FOR CARRYING OUT THE INVENTION

Figure 1:
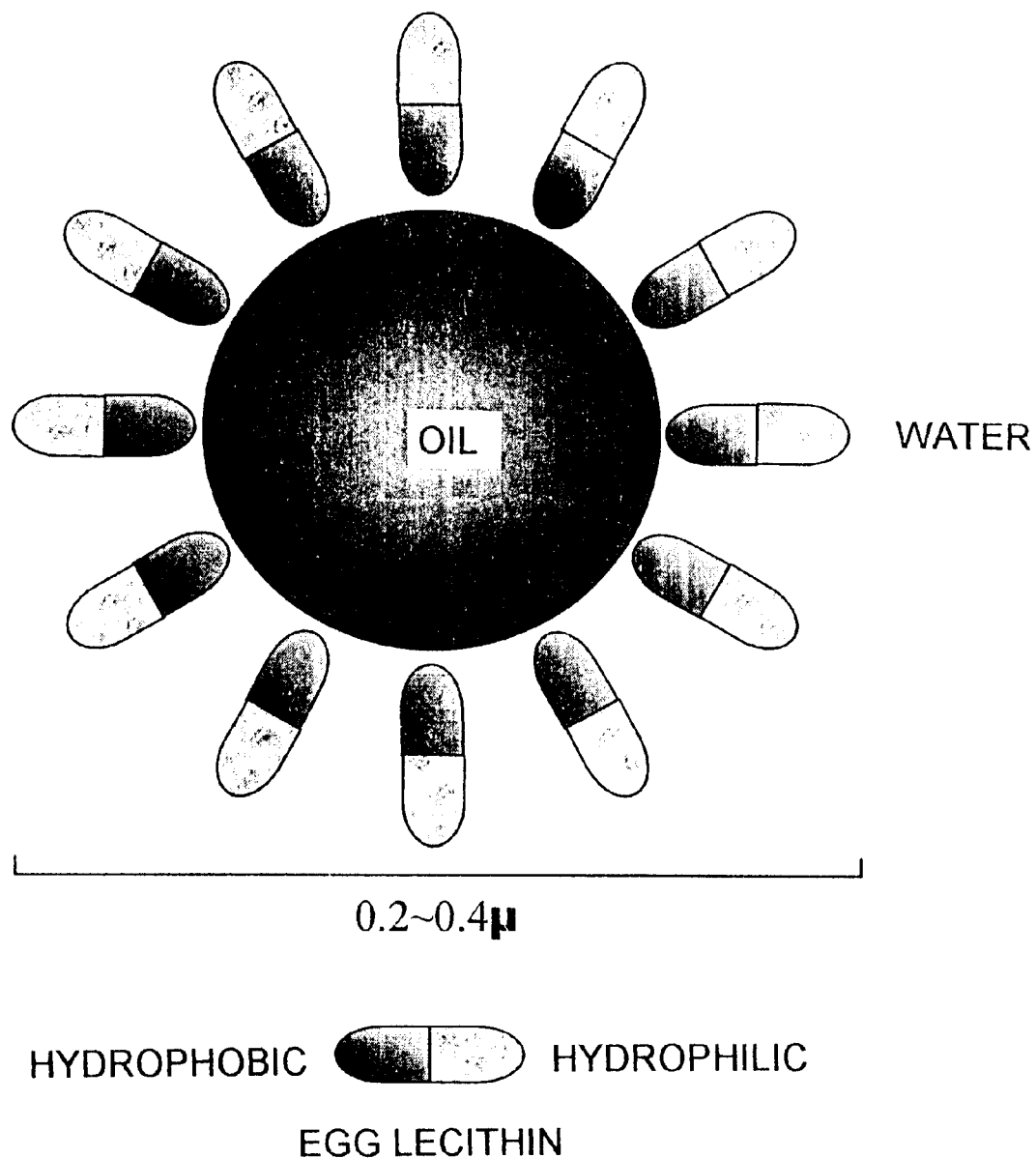
FIG. 1 is an illustration representing the egg lecithin-coated Propofol emulsion.
Figure 2:
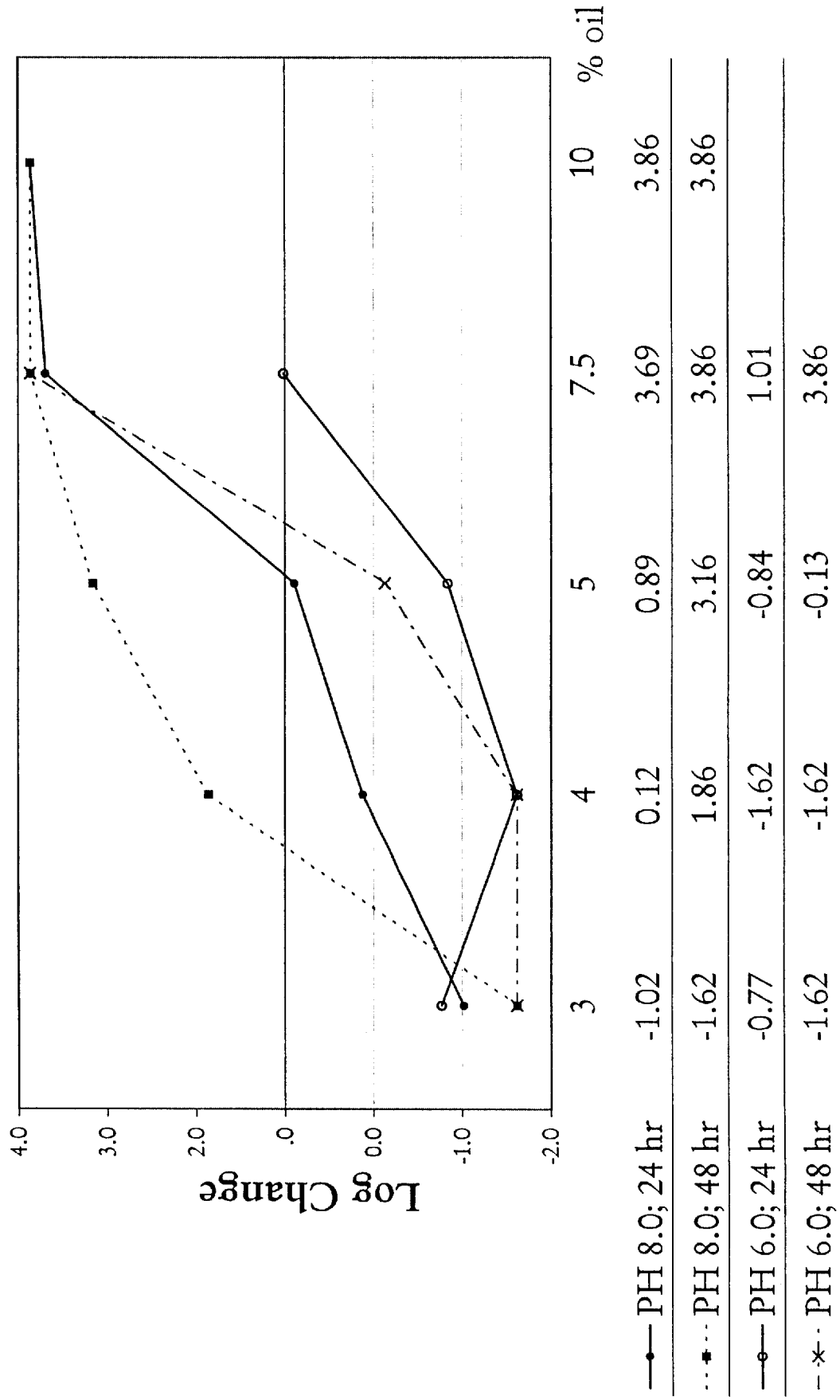
FIG. 2 a graph illustrating how the amount of soybean oil and pH in the Propofol formulation affects the growth of *C. Albicans* after incoculating at 24 and 48 hours. Also, the difference in microbial growth at pH-6 and pH-8 is shown.
Figure 3:
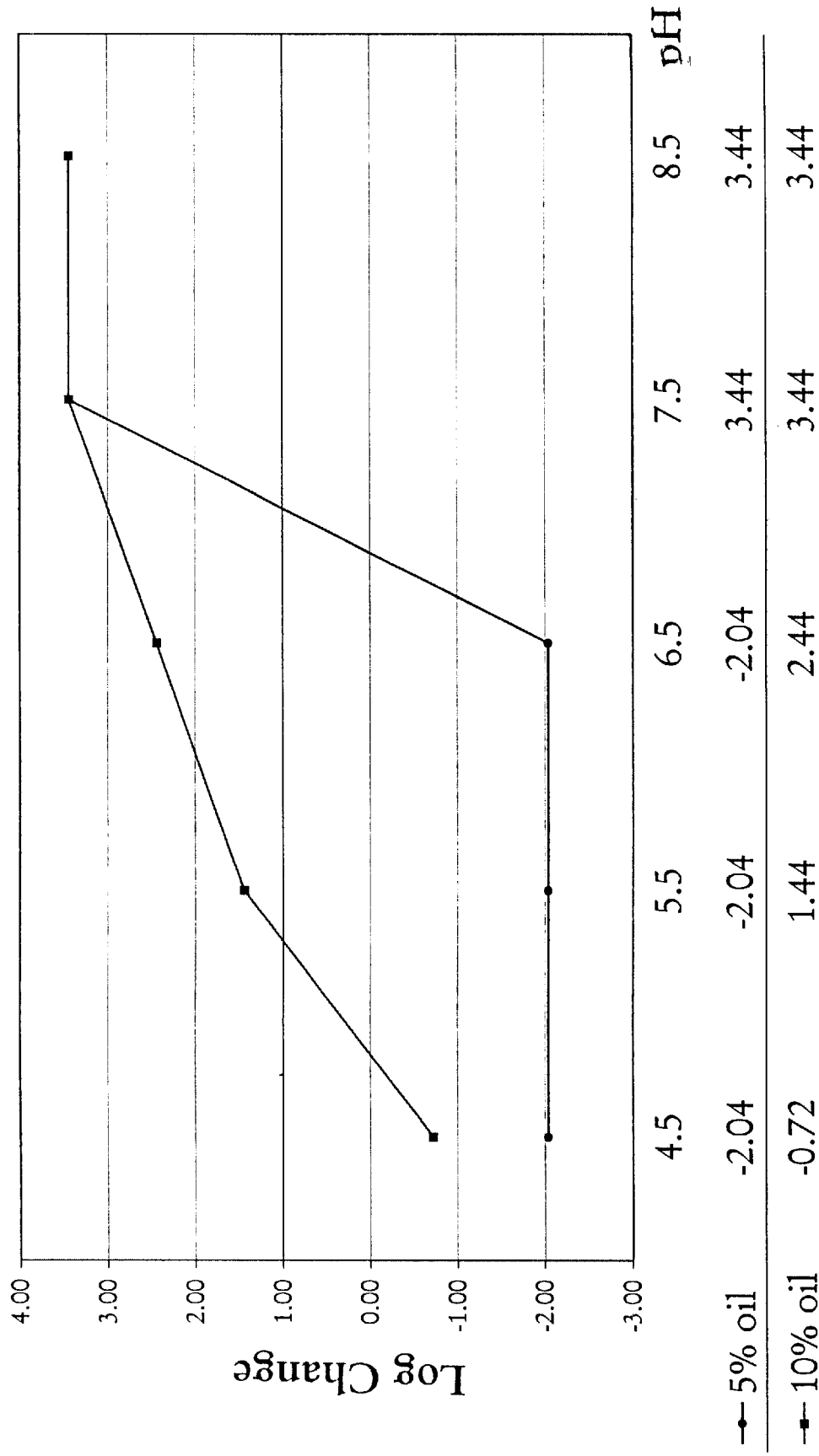
FIG. 3 is a graph illustrating how the pH in the Propofol formulation affects the growth of *Escherichia Coli* after inoculating at 24 and 4hours. Also the difference in microbial growth between 5% and 10% of soybean oil is shown.
Figure 4:
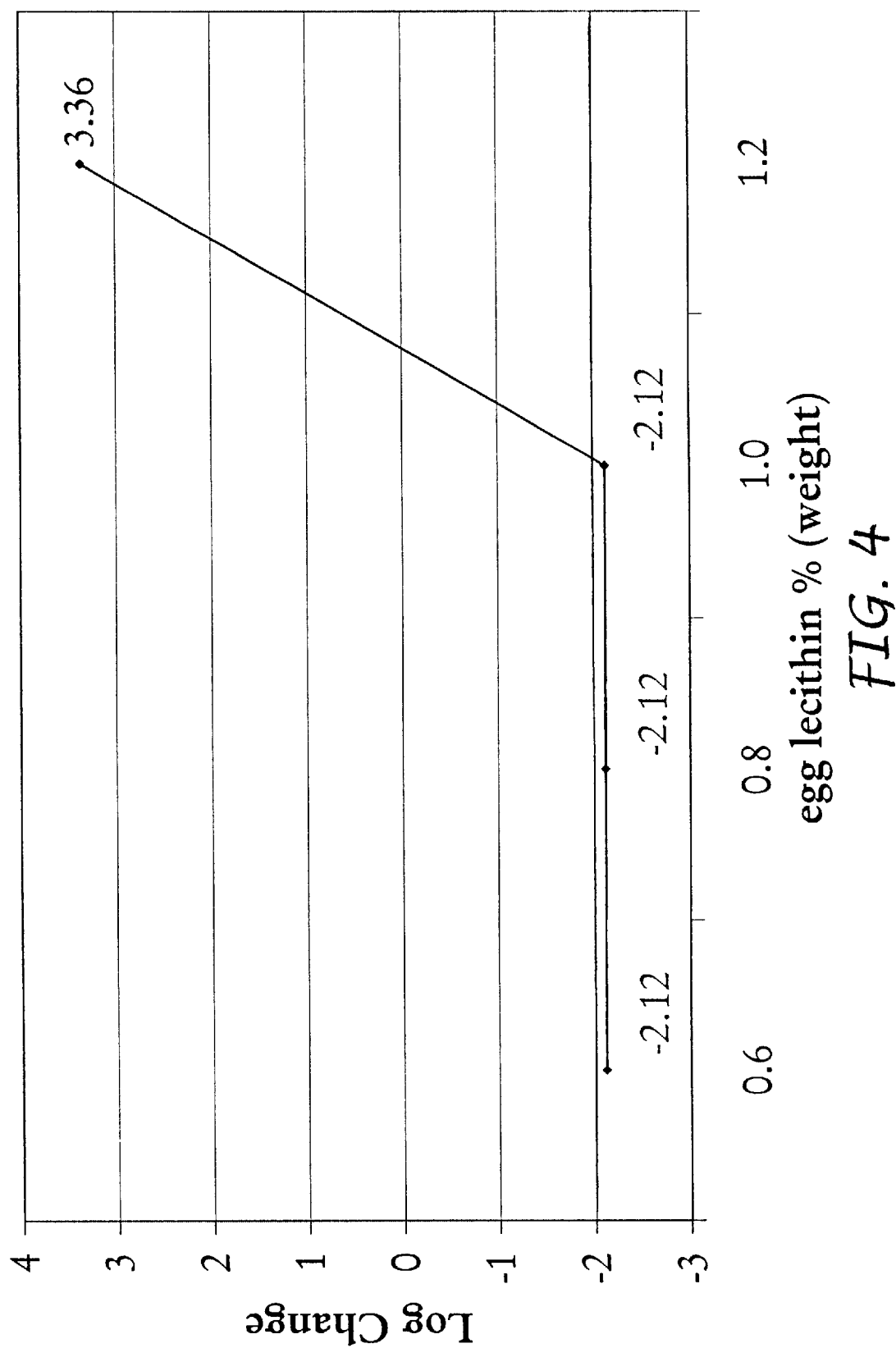
FIG. 4 is a graph illustrating how the amount of egg lecithin in the Propofol formulation affects the growth of *Escherichia Coli* after incoculating at 24 and 48 hours.

The invention is a sterile pharmaceutical composition for parenteral administration comprised of an oil-in-water emulsion, in which Propofol is dissolved in a water-immiscible solvent, preferably soybean oil, and stabilized by a surfactant, preferably egg lecithin. The composition further comprises a reduced amount of egg lecithin and soybean oil, and which furthermore comprises a low pH range to inhibit micorbial contamination during IV infusions over a period of time.

An oil-in-water emulsion is meant to be a distinct, two-phase system that is in equilibrium and in effect, as a whole, is kinetically stable and thermodynamically unstable.

Prevention of a significant growth of microorganisms is meant to be growth of microorganisms, which is preferably no more than a one log increase following extrinsic contamination generally found in treatment settings such as ICU's and the like. For purposes of this definition, the contamination is commonly about 50–200 colony forming units/mL at a temperature in the range of 20–25° C.

The formulation of the present invention typically comprises from 0.1% to 5% by weight of Propofol, and, more preferably from 1 to 5% Propofol, preferably, the formulation comprises 1%, 2% or 5% Propofol.

The water-immiscible solvent is suitably present in an amount that is preferably from 3 to 10% by weight of the composition, and more preferably from 3 to 6% by weight of the composition for the formulation containing 1 or 2% of Propofol, and from 6 to 10% by weight of the composition for the formulation with of Propofol.

The oil-in-water emulsion may be Prepared by dissolving Propofol in a water-immiscible solvent, and preparing an aqueous phase containing a surfactant and other water-soluble ingredients, and then mixing the oil with the aqueous phase. The crude emulsion is homogenized under high pressure to provide an ideal emulsion.

A wide range of water-immiscible solvents can be used in the composition of the present invention. Typically, the water-immiscible solvent is a vegetable oil, for example, soybean, safflower, cottonseed, corn, sunflower, arachis, castor or olive oil. Preferably, the vegetable oil is soybean oil. Alternatively, the water-immiscible solvent is an ester of a medium or long-chain fatty acid, for example a mono-, di-, or triglyceride, or is a chemically modified or manufactured palmitate, glyceral ester or polyoxyl, hydrogenated castor oil. In a further alternative, the water-immiscible solvent may be a marine oil, for example cod liver or other fish-derived oil. Suitable solvents also include fractionated oils, for example, fractionated coconut oil, or modified soybean oil. Furthermore, the composition of the present invention may comprise a mixture of two or more of the above water-immiscible solvents.

The composition of the present invention comprises a pharmaceutically acceptable surfactant to provide a stable emulsion. The surfactant is suitably present in an amount that is no more than 1% by weight of the composition for the formulation containing 3 to 6% of water-immiscible solvent, and more preferably is 0.2 to 1.0% by weight of the composition, preferably is 0.66% by weight of the composition. For the formulation containing 6 to 10% of water-immiscible solvent, a suitable amount of surfactant is no more than 2% by weight of the composition, and preferably is 0.6 to 2% by weight of the composition, and more preferably is 1.2% by weight of the composition. Suitable surfactants include synthetic non-ionic surfactant such as ethoxylated eithers and esters and polypropylene-polyethylene block co-polymers, and phosphatides, for example naturally occurring phosphatides such as egg and soya phosphatides and modified or artificially manipulated phosphatides (for example those prepared by physical fractionation and/or chromatography), or mixture thereof. Preferred surfactants are egg and soya phosphatides. Most preferred is egg lecithin.

The composition of the present invention is suitably formulated to have a pH range of 4.5 to 9.0, and preferably the formulation has a pH range 5.0–7.5. The pH may be adjusted as required by means of addition of an alkali, for example sodium hydroxide, or an acid, for example hydrochloric acid.

The composition of the present invention may be made isotonic with blood by incorporation of a suitable tonicity modifier, for example glycerin.

The composition of the present invention comprises a pharmaceutically acceptable carrier. The carrier is preferably a pyrogen-free water or water for injection U.S.P.

The present invention's composition is a sterile aqueous formulation and is prepared by standard manufacturing techniques using, for example, aseptic manufacture or terminal sterilization by autoclaving.

The compositions of the present invention are useful as anesthetics, which include sedation, induction and maintenance of general anesthesia. Accordingly, in another aspect, the present invention provides a method of producing anesthesia (including sedation, induction and maintenance of general anesthesia) in a warm-blooded animal, including humans.

Producing anesthesia comprises administering parenterally a sterile, aqueous pharmaceutical composition which comprises an oil-in-water emulsion in which Propofol in a water-immiscible solvent is emulsified with water and a surfactant. A preferred composition has been described in examples below.

Typically, dosage levels of Propofol for producing general anesthesia are from, about 2.0–2.5 mg/kg for an adult. Dosage for maintenance of anesthesia is generally about 4–12 mg/kg/hr. Sedative effects may be achieved with, for example, a dosage of 0.3–4.5 mg/kg/hr. Dosage levels of Propofol for producing general anesthesia, induction and maintenance, and for producing a sedative effect, may be derived from the substantive literature and may be determined by one skilled in the art of to suit a given patient and treatment regime.

Accordingly, in one aspect, the present invention provides an optimized formulation that comprises a sufficiently low amount of egg lecithin which is reduced from the industry standard of 1.2% by weight to about 0.6% by weight. In another aspect; the present invention provides a formulation that comprises a low amount of soybean oil, which is decreased from the industry standard of 10% by weight to 3–6% by weight. In yet another aspect, the present invention provides a formulation with a lower pH range, which is changed from the industry standard of pH 7.0–8.5 to pH 5.0–7.5

In accordance with the present invention several advantages have been found, which include, no more than a ten-fold increase in the growth of microorganism, such as *S. aureus, E. coli, P. aeruginosa* and *C. albicans* for at least 24 hours.

Another useful aspect of the present invention arises from administering the subject formulation to hyperlipidemia patient, in that the low amount of fat thereof places them at lower risk of triglyceridemia.

EXAMPLE 1

Preferred composition is as follows:

| Components | Quantities % (weight) |
|---|---|
| Propofol | 1.0 |
| soybean oil | 3.0–6.0 |
| egg lecithin | 0.2–1.0 |
| glycerin | 2.25 |
| sodium hydroxide | q.s. |
| water for injection | to 100 |
| pH | 5.0–7.5 |

The production process is carried out under nitrogen, and weights refer to weight in the final volume.

A sterile, aqueous oil-in-water emulsion for parenteral administration was prepared as follows:

1. The aqueous phase is prepared by adding lecithin and glycerin into water for injection at about 20° C.–60° C. and mixed until a uniform dispersion was achieved.
2. The oil phase is prepared by adding Propofol to soybean oil and 'stirred until dissolved at about 20° C.–60° C.
3. The oil phase is added to the aqueous phase, mixed and pH adjusted with sodium hydroxide, then mixed to form the crude emulsion.
4. The crude emulsion is microfluidized until the target globule size is reached.
5. The pH of the emulsion is adjusted if necessary. The final emulsion is filtered into a holding vessel.
6. The final emulsion is then filled into containers under nitrogen and autoclaved.

An oil-in-water emulsion containing 2% or 5% by weight of Propofol may be prepared in a similar manner using the quantities of ingredients as shown in Example 2 or Example 3:

EXAMPLE 2

| Components | Quantities % (weight) |
|---|---|
| Propofol | 2.0 |
| soybean oil | 3.0–6.0 |
| egg lecithin | 0.2–1.0 |
| glycerin | 2.25 |
| sodium hydroxide | q.s. |
| water for injection | to 100 |
| pH | 5.0–7.5 |

EXAMPLES 3

| Components | Quantities % (weight) |
|---|---|
| Propofol | 5.0 |
| soybean oil | 6.0–10.0 |
| egg lecithin | 1.2 |

-continued

| Components | Quantities % (weight) |
|---|---|
| glycerin | 2.25 |
| sodium hydroxide | q.s. |
| water for injection | to 100 |
| pH | 5.0–7.5 |

MICROBIOLOGICAL ACTIVITY

Oil-in-water formulations of Propofol containing various ingredients were prepared as described above. Approximately 50–200 colony forming units (CFU) per ml of four standard U.S.P. organisms *S. Aureus* (ATCCF 6538) *E. coli* (ATCC 8739), *P. aeruginosa* (ATCC 9027) and *C. albicans* (ATCC 10231) for preservative efficacy tests[14] were inoculated in each formulation and incubated at 20–25° C. The viable count of the test organism was determined after 24 and 48 hours.

The antimicrobial effects of the Propofol composition containing low egg lecithin and soybean oil concentration with a lowered pH are illustrated in the following tables. These effects are contrasted with other Propofol formulation including 1.2% egg lecithin, 10% soybean oil emulsion and the Propofol formulation comprising 0.005% EDTA and marketed under tradename DIPRIVAN[(R)]. These results indicate that the formulation with the lower amount of egg lecithin and soybean oil, and with a lower pH is effective in preventing a not more than 10-fold increase in growth of microorganisms for 24 hours after microbial contamination.

TABLE 1

Comparison of microbial Growth against *S. aureus*

| Formulation (%) | | | | Microbial Growth (log cfu/mL) | | | | | | | | | |
|---|---|---|---|---|---|---|---|---|---|---|---|---|---|
| | | | | PH = 4.5 | | PH ÷ 5.5 | | PH = 6.5 | | PH = 7.5 | | PH = 8.5 | |
| Propofol | Soybean Oil | Egg Lecithin | Inoculated No. | 24 hr | 48 hr | 24 hr | 48 hr | 24 hr | 48 hr | 24 hr | 48 hr | 24 hr | 48 hr |
| 1 | 3 | 0.6 | 1.64 | 0 | 0 | 0 | 0 | 0.7 | 0 | 0.7 | 0.3 | 0.3 | 0 |
| 1 | 4 | 0.6 | 1.64 | 0 | 0 | 0.3 | 0 | 1.44 | 1.26 | 1.58 | 1.26 | 1.74 | 0.91 |
| 1 | 5 | 0.6 | 1.63 | 0 | 0 | 0.3 | 0.3 | 0 | 1.75 | 1.83 | 1.99 | 1.65 | 1.76 |
| 2 | 5 | 0.6 | 1.64 | 0 | 0 | 0 | 0 | 0 | 0 | 0 | 0 | 0 | 0 |
| 2 | 4 | 0.6 | 1.64 | | | 0 | 0 | | | | | 0 | 0 |
| 1 | 3 | 1.2 | 1.64 | | | | | | | 0.78 | 0.6 | | |
| 1 | 10 | 1.2 | 1.64 | | | | | | | 2.95 | >5.47 | | |
| 1 | 10 | 1.2 | 1.71 | | | | | | | 3.34 | >3.77 | | |
| 1 | 10 | 1.2 | 1.64 | | | | | | | 0 | 0 | | |
| | Diprivan | | 1.71 | | | | | | | 0 | 0 | | | o signifies that all *S. Aureus* died.

TABLE 2

Comparison of microbial Growth against *P. aeruginosa*

| Formulation (%) | | | | Microbial Growth (log cfu/mL) | | | | | | | | | |
|---|---|---|---|---|---|---|---|---|---|---|---|---|---|
| | | | | PH = 4.5 | | PH ÷ 5.5 | | PH = 6.5 | | PH = 7.5 | | PH = 8.5 | |
| Propofol | Soybean Oil | Egg Lecithin | Inoculated No. | 24 hr | 48 hr | 24 hr | 48 hr | 24 hr | 48 hr | 24 hr | 48 hr | 24 hr | 48 hr |
| 1 | 3 | 0.6 | 2.09 | 0 | 0 | 0 | 0 | 0 | 0 | 0 | 0 | 0 | 0 |
| 1 | 4 | 0.6 | 2.09 | 0 | 0 | 0 | 0 | 0 | 0 | 0 | 0 | 0 | 0 |
| 1 | 5 | 0.6 | 2.09 | 0 | 0 | 0 | 0 | 0 | 0 | 0 | 0 | 0 | 0 |
| 2 | 5 | 0.6 | 2.09 | 0 | 0 | 0 | 0 | 0 | 0 | 0 | 0 | 0 | 0 |
| 2 | 4 | 0.6 | 2.09 | | | 0 | 0 | | | | | 0 | 0 |
| 1 | 3 | 1.2 | 2.09 | | | | | | | 0 | 0 | | |
| 1 | 10 | 1.2 | 2.09 | | | | | | | >5.48 | >5.48 | | |
| 1 | 10 | 1.2 | 1.86 | | | | | | | >5.48 | >5.48 | | |
| 5 | 10 | 1.2 | 2.09 | | | | | | | 0 | 0 | | |
| | Diprivan | | 1.86 | | | | | | | 0.85 | 1.56 | | | o signifies that all *P. Aeruginosa* died.

TABLE 3

Comparison of microbial Growth against *Escherichia Coli*

| | | | | Microbial Growth (log cfu/mL) | | | | | | | | | | |
|---|---|---|---|---|---|---|---|---|---|---|---|---|---|---|
| Formulation (%) | | | | PH = 4.5 | | PH = 5.5 | | PH = 6.5 | | PH = 7.5 | | PH = 8.5 | | |
| Propofol | Soybean Oil | Egg Lecithin | Inoculated No. | 24 hr | 48 hr | 24 hr | 48 hr | 24 hr | 48 hr | 24 hr | 48 hr | 24 hr | 48 hr |
| 1 | 3 | 0.6 | 2.31 | 0 | 0.3 | 0 | 0 | 0 | 0 | 0 | 0 | 0 | 0 |
| 1 | 4 | 0.6 | 2.31 | 0 | 0 | 1 | 0 | 0.91 | 0.6 | 0.3 | 0 | 0 | 0 |
| 1 | 5 | 2.6 | 2.31 | 0 | 0 | 0.8 | 0.6 | 1.23 | 0.78 | 1.04 | 0.3 | 0.7 | 0 |
| 2 | 5 | 0.6 | 2.31 | 0 | 0 | 0 | 0 | 0 | 0 | 0 | 0 | 0 | 0 |
| 2 | 4 | 0.6 | 2.31 | | | 0 | 0 | | | | | 0 | 0 |
| 1 | 3 | 1.2 | 2.12 | | | | | | | >5.48 | >5.48 | | |
| 1 | 10 | 1.2 | 2.31 | | | | | | | >5.68 | 3.48 | | |
| 1 | 10 | 1.2 | 1.98 | | | | | | | >5.48 | >5.48 | | |
| 5 | 10 | 1.2 | 2.31 | | | | | | | 0 | 0 | | |
| Diprivan | | | 1.98 | | | | | | | 1.28 | 1.11 | | | o signifies that all *E. Coli* died.

TABLE 4

Comparison of microbial Growth against *C. albicans*

| | | | | Microbial Growth (log cfu/mL) | | | | | | | | | | |
|---|---|---|---|---|---|---|---|---|---|---|---|---|---|---|
| Formulation (%) | | | | PH = 4.5 | | PH = 5.5 | | PH = 6.5 | | PH = 7.5 | | PH = 8.5 | | |
| Propofol | Soybean Oil | Egg Lecithin | Inoculated No. | 24 hr | 48 hr | 24 hr | 48 hr | 24 hr | 48 hr | 24 hr | 48 hr | 24 hr | 48 hr |
| 1 | 3 | 0.6 | 1.66 | 0 | 0 | 0 | 0 | 0 | 0 | 0 | 0 | 0 | 0 |
| 1 | 4 | 0.6 | 1.66 | 0 | 0 | 0 | 0 | 0 | 0 | 0 | 0 | 0 | 0 |
| 1 | 5 | 0.6 | 1.66 | 0 | 0 | 0 | 0 | 0 | 0 | 0.81 | 0 | 0 | 0.51 |
| 2 | 5 | 0.6 | 1.66 | 0 | 0 | 0 | 0 | 0 | 0 | 0 | 0 | 0 | 0 |
| 2 | 4 | 0.6 | 1.66 | | | 0 | 0 | | | | | 0 | 0 |
| 1 | 3 | 1.2 | 1.66 | | | | | | | 0 | 0 | | |
| 1 | 10 | 1.2 | 1.66 | | | | | | | >5.47 | >5.47 | | |
| 1 | 10 | 1.2 | 1.76 | | | | | | | >5.38 | >5.38 | | |
| 5 | 10 | 1.2 | 1.66 | | | | | | | 0 | 0 | | |
| Diprivan | | | 1.76 | | | | | | | 1 | 0 | | | o signifies that all *C. Albicans* died.

In view of the above data it is deemed that the formulations of the present invention have the advantages as disclosed and claims.

While the invention has been described in complete detail and pictorially shown in the accompanying drawings it is not to be limited to such details, since many changes and modifications may be made to the invention without departing from the spirit and the scope thereof. For example, the compositions and manufacturing processes disclosed are exemplary, hence, it is described to cover any and all modifications and forms which may come within the language and scope of the claims.

What is claimed is:

1. A sterile pharmaceutical composition for parenteral administration of Propofol, wherein said Propofol is:
   a) dissolved in a low amount of water-immiscible solvent,
   b) emulsified with water for injection, and
   c) stabilized in a 0.2–1.0% by weight of a surfactant having a pH range to prevent a no more than a 10-fold increase in the growth of each of *Pseudomonas aeruginosa, Escherichia coli, Staphylococcus aureus* and *Candida albicans* for at least 24 hours after adventitious, extrinsic contamination.

2. The sterile pharmaceutical composition as specified in claim 1 wherein the Propofol composition contains 3–6% by weight of a water-immiscible solvent.

3. The sterile pharmaceutical composition as specified in claim 2 wherein the water-immiscible solvent is a vegetable oil or an ester of a fatty acid.

4. The sterile pharmaceutical composition as specified in claim 3 wherein the water-immiscible solvent is soybean oil.

5. The sterile pharmaceutical composition as specified in claim 1 wherein the pH is between 5.0–7.0.

6. The sterile pharmaceutical composition as specified in claim 1 wherein the surfactant is a naturally occurring phosphatide.

7. The sterile pharmaceutical composition as specified in claim 5 wherein the naturally occurring phosphatide is comprised of egg lecithin.

8. The sterile pharmaceutical composition as specified in claim 1 wherein the surfactant is a non-naturally occurring phosphatide.

9. The sterile pharmaceutical composition as specified in claim 1 which is isotonic with blood.

10. The sterile pharmaceutical composition as specified in claim 9 which is istonic with blood by incorporation of glycerin.

11. The sterile pharmaceutical composition as specified in claim 1 wherein the Propofol is added at 1% to 2% by weight.

12. A sterile pharmaceutical composition in the form of an oil-in-water emulsion comprising:
   a) about 1% by weight of Propofol,
   b) 3–6% by weight of soybean oil,
   c) 0.2–1.0% by weight of egg lecithin,
   d) about 2.25% by weight of glycerin, e) sodium hydroxide, f) water to 100%, and g) pH between 5.0–7.5.

13. A sterile pharmaceutical composition in the form of an oil-in-water emulsion comprising:

a) about 2% by weight of Propofol, b) 3–6% by weight of soybean oil, c) 0.2–1.0% by weight of egg lecithin, d) about 2.25% by weight of glycerin, e) sodium hydroxide, f) water to 100%, and g) pH between 5.0 and 7.5.

14. The sterile pharmaceutical composition as specified in claim 12 wherein the water is water for injection U.S.P.

* * * * *